United States Patent [19]

Jaynes

[11] Patent Number: 5,677,287
[45] Date of Patent: Oct. 14, 1997

[54] ANTIBACTERIAL 16-MEMBERED RING MACROLIDES CONTAINING OLEFINS AT C-20

[75] Inventor: Burton Humphrey Jaynes, Ivoryton, Conn.

[73] Assignee: Pfizer Inc., New York, N.Y.

[21] Appl. No.: 513,808

[22] PCT Filed: Jan. 6, 1994

[86] PCT No.: PCT/US94/00095

§ 371 Date: Sep. 11, 1995

§ 102(e) Date: Sep. 11, 1995

[87] PCT Pub. No.: WO94/21657

PCT Pub. Date: Sep. 29, 1994

Related U.S. Application Data

[63] Continuation of Ser. No. 145,456, Oct. 29, 1993, abandoned, which is a continuation-in-part of Ser. No. 32,901, Mar. 18, 1993, abandoned.

[51] Int. Cl.⁶ .............................. A61K 31/70; C07H 17/08
[52] U.S. Cl. .................................. 514/30; 536/7.1
[58] Field of Search ........................ 536/7.1; 514/30

[56] References Cited

U.S. PATENT DOCUMENTS

| | | | |
|---|---|---|---|
| 4,920,103 | 4/1990 | Kirst et al. | 514/30 |
| 4,921,947 | 5/1990 | Tao et al. | 536/7.1 |
| 5,545,624 | 8/1996 | Hecker et al. | 514/30 |

FOREIGN PATENT DOCUMENTS

| | | |
|---|---|---|
| 100645 | 2/1984 | European Pat. Off. |
| 228264 | 7/1987 | European Pat. Off. |
| 394135 | 10/1990 | European Pat. Off. |
| 61-129195 | 6/1986 | Japan. |
| 61-191692 | 8/1986 | Japan. |
| 03261797 | 11/1991 | Japan. |
| 2135670 | 9/1984 | United Kingdom. |

OTHER PUBLICATIONS

H. A. Kirst et al., J. of Antibiotics, vol. XL, No. 6, 1987, pp. 823–842.

K. Funaishi et al., J. of Antibiotics, vol. XLIII, No. 8, 1990, pp. 938–947.

A. Tanaka et al., J. of Antibiotics, vol. XXXIV, No. 10, 1981, pp. 1374–1376.

*Primary Examiner*—Elli Peselev
*Attorney, Agent, or Firm*—P. C. Richardson; Gregg C. Benson; John D. Conway

[57] ABSTRACT

The present invention relates to C-20 olefin derivatives of 16-membered macrolide antibiotics repromicin, rosaramicin, 5-mycaminosyltylonolide, desmycosin, lactenocin, O-demethyllactenocin, 4'-deoxymycaminosyltylonolide and 23-deoxymycaminosyltylonolide, which are useful against bacterial and mycoplasmic pathogens in animals. Also claimed are a pharmaceutical composition of such derivatives and their use in treating bacterial and mycoplasmic infections in animals.

20 Claims, No Drawings

ANTIBACTERIAL 16-MEMBERED RING MACROLIDES CONTAINING OLEFINS AT C-20

CROSS REFERENCE TO RELATED APPLICATIONS

This application is the national stage of PCT application number PCT/US94/00095 having an international filing date of Jan. 6, 1994, which is a continuation of U.S. application Ser. No. 08/145,456, filed Oct. 29, 1993, now abandoned, which is a continuation-in-part of U.S. application Ser. No. 08/032,901, filed Mar. 18, 1993, now abandoned.

BACKGROUND OF THE INVENTION

This invention is concerned with new antibiotics. In particular, this invention relates to compounds which are derivatives of the macrolide antibiotics repromicin, rosaramicin, 5-mycaminosyltylonolide, desmycosin, lactenocin, O-demethyllactenocin, 4'-deoxymycaminosyltylonolide and 23-deoxymycaminosyltylonolide; to the pharmaceutically-acceptable acid addition salts of such derivatives; to a method of using such derivatives in the treatment of illnesses in animals caused by bacterial and mycoplasmic pathogens; and to pharmaceutical compositions useful therefor. The term "animals" includes mammals, fish and birds.

There are numerous agents known to combat bacterial infectious diseases in animals, but for many specific diseases the current agents of choice leave much to be desired. In some instances the agents may not persist long enough in the host and, therefore, require frequent dosing to maintain therapeutically effective blood and/or tissue levels. For meat producing animals (cattle, poultry, sheep and swine) this will require considerable labor intensive animal handling which is costly to the producer. In other cases, the agent may be poorly tolerated or even toxic to the host at therapeutically effective doses. Agents with increased potency, a longer half-life, an increased therapeutic index and a broader spectrum of antibacterial activity as well as agents with greater oral absorption would improve the scope of animal diseases that could be more effectively treated. Thus, the need for new antibacterial and anti-mycoplasmic agents with improved properties endures.

Diseases of particular concern are: bovine respiratory disease, the principal causative bacterial pathogens of which are *Pasteurella haemolytica, P. multocida* and *Haemophilus somnus;* pasteurellosis in swine, goats, sheep and poultry (*P. multocida*); swine pleuropneumonia (*Actinobacillus pleuropneumoniae*); swine streptococcus infections (*Streptocoocus suis*); and for all of the above mentioned hosts, infections by *Mycoplasma spp*.

Derivatives of tylosin and its related macrolides have been shown to be effective against infections in poultry, cattle and pigs caused by certain gram-positive and gram-negative bacteria: Kirst et el., U.S. Pat. No. 4,920,103; Tao et el., U.S. Pat. No. 4,921,947; Kirst et el., U.K. Patent Application GB 2135670A. C-20 reductive amination products of the above macrolides are disclosed in copending U.S. patent applications, Ser. No. 07/914,242, filed Jul. 15, 1992, and Ser. No. 07/996,243, filed Dec. 23, 1993.

SUMMARY OF THE INVENTION

This invention is concerned with new antibiotics which are derivatives of the macrolides repromicin, rosaramicin, 5-mycaminosyltylonolide, desmycosin, lactenocin, O-demethyllactenocin, 4'-deoxymycaminosyltylonolide and 23-deoxymycaminosyltylonolide and to the acid addition salts of such derivatives. These new antibiotics have enhanced potency against bacterial pathogens over the parent compounds and are active against mycoplasmic pathogens.

The compounds of the present invention and their pharmaceutically-acceptable salts are of the formula I

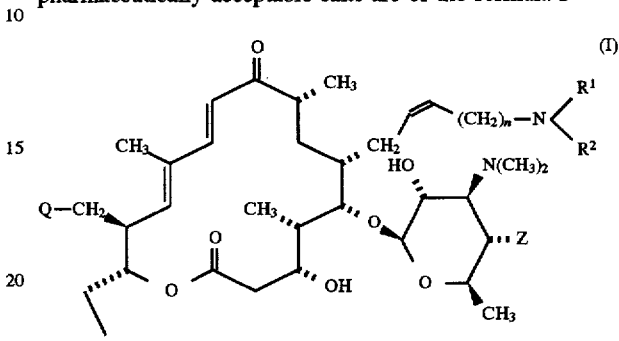

or the formula II

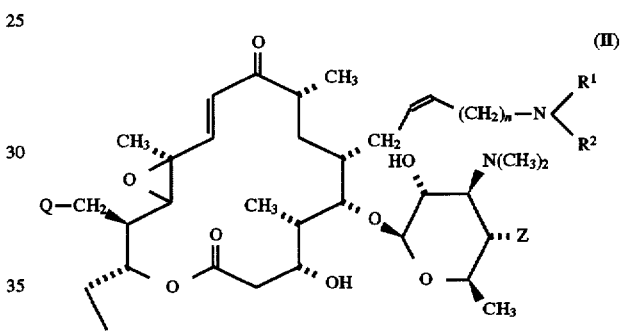

and the pharmaceutically-acceptable salts thereof wherein n is an integer from 1 to 4;

Z is H or OH;

Q is selected from the group consisting of H, OH, fluoro, chloro, bromo, iodo, $OX^1$, $SX^1$,

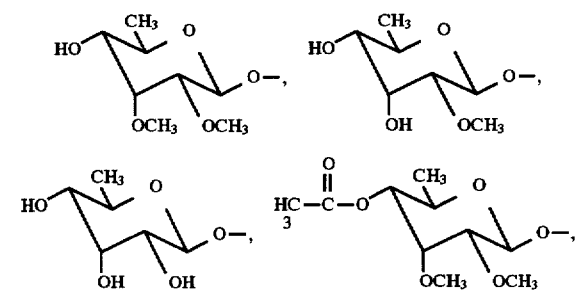

azetidin-1 -yl, pyrrolidin-1 -yl, piperidin-1 -yl, 3,3-dimethylpiperidin-1 -yl, hexahydroazepin-1 -yl, octahydroazocin-1 -yl, octahydroindol-1 -yl, 1,3,3a,4,7,7a-hexahydroisoindol-2-yl, decahydroquinol-1 -yl, decahydroisoquinol-2-yl, 1,2,3,4-tetrahydroisoquinol-2-yl, 1,2,3,6-tetrahydropyridin-1-yl, 4-alkylpiperazin-1-yl having 1 to 4 carbons in the alkyl portion, morpholine, 2,6-dimethylmorpholin4-yl, thiomorpholino, and

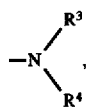

where $R^3$ and $R^4$ are independently selected from the group consisting of H, alkyl having 1 to 4 carbons, hydroxyalkyl having 2 to 4 carbons, cycloalkyl having 3 to 8 carbons, alkenyl having 3 to 4 carbons, optionally substituted benzyl, alkoxyalkyl having 1 to 4 carbons in the alkoxy portion and 2 to 4 carbons in the alkyl portion and alkoxyalkoxyalkyl having 1 to 4 carbons in each of the alkoxy portions and 2 to 4 carbons in the alkyl portion, and

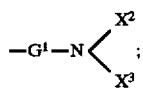

wherein the optionally substituted benzyl is optionally substituted with 1 to 5 substituents selected from the group consisting of $(C_1-C_4)$alkyl, $(C_1-C_4)$alkoxy, fluoro, chloro, bromo, iodo, nitro, amine, cyano, hydroxy, trifluoromethyl and carboalkoxy having 1 to 4 carbons;

$G^1$ is $(C_2-C_4)$alkylene; and $X^2$ and $X^3$ are independently selected from the group consisting of hydrogen, alkyl having 1 to 4 carbons, cycloalkyl having 3 to 8 carbons, and alkoxyalkyl having 2 to 4 carbons in the alkyl portion and 1 to 4 carbons in the alkoxy portion;

or $X^2$ and $X^3$ are taken together with the nitrogen to which they are attached and form a cyclic amine having 3 to 6 carbon atoms;

$X^1$ is selected from the group consisting of optionally substituted alkyl having 1 to 4 carbons, optionally substituted cycloalkyl having 4 to 8 carbons and an optionally substituted group consisting of phenyl, benzyl, pyridinyl, quinolinyl, isoquinolinyl, quinazolinyl, pyrimidinyl, imidazolyl, oxazolyl, thiazolyl, benzimidazolyl, indolyl, benzoxazolyl and benzthiazolyl;

wherein the optionally substituted alkyl and optionally substituted cycloalkyl can be optionally substituted with 1 or 2 substituents independently selected from the group consisting of hydroxy, amino, N-alkylamino having 1 to 4 carbons, N,N-dialkylamino having a total of 2 to 6 carbons and alkoxy having 1 to 4 carbons; and where the optionally substituted group consisting of phenyl, benzyl, pyridinyl, quinolinyl, isoquinolinyl, imidazolyl, oxazolyl, thiazolyl, benzimidazolyl, indolyl, benzoxazolyl and benzthiazolyl is optionally substituted with 1 to 3 substituents independently selected from the group consisting of alkyl having 1 to 4 carbons, fluoro, chloro, bromo, amino, nitro, cyano, trifluoromethyl, N-alkylamino having 1 to 4 carbons, N,N-dialkylamino having a total of 2 to 6 carbons, carboxyl, carboalkoxy having 1 to 4 carbons, carboxamido and sulfonamido;

$R^1$ is selected from the group consisting of hydrogen, an aminoacyl group, a dipeptidyl group, alkenyl having 3 to 5 carbons provided that the double bond is not adjacent to the nitrogen to which $R^1$ is attached, alkynyl having 3 to 5 carbons provided that the triple bond is not adjacent to the nitrogen to which $R^1$ is attached, hydroxyalkyl having 2 to 4 carbons in the alkyl portion, optionally substituted alkyl having 1 to 4 carbons, optionally substituted benzyl, optionally substituted cycloalkyl having 3 to 7 carbons, and alkoxyalkyl having 2 to 4 carbons in the alkyl portion and 1 to 4 carbons in the alkoxy portion;

wherein the optionally substituted benzyl is optionally substituted with 1 to 5 substituents selected from the group consisting of $(C_1-C_4)$alkyl, $(C_1-C_4)$alkoxy, fluoro, chloro, bromo, iodo, nitro, amino, cyano, hydroxy, trifluoromethyl and carboalkoxy having 1 to 4 carbons;

the optionally substituted alkyl and optionally substituted cycloalkyl are optionally substituted with cyano, N-alkylamino having 1 to 5 carbons and N,N-dialkylamino having a total of 2 to 6 carbons; and the aminoacyl group and the aminoacyl groups of the dipeptidyl group are independently selected from the group consisting of the D- or L- form, when applicable, of alanyl, arginyl, asparagyl, aspartyl acid, cysteinyl, cystyl, glutamyl acid, glutamyl, glycyl, histidyl, hydroxyllysyl, hydroxyprolyl, isoleucyl, leucyl, lysyl, methionyl, phenylalanyl, prolyl, seryl, threonyl, tryptophyl, tyrosyl, valyl, β-alanyl, β-lysyl, N,N-dimethylglycyl, α,α-dimethylglycyl, α-aminobutyryl, 4-hydroxyphenylglycyl, phenylglycyl, α,γ-diaminobutyryl, ornithyl, homoseryl, bicyl, N,N-diethyl-β-alanyl, N,N-dimethyl-γ-aminobutyryl and sarcosyl;

$R^2$ is selected from the group consisting of hydrogen, alkenyl having 3 to 5 carbons provided that the double bond is not adjacent to the nitrogen to which $R^1$ is attached, alkynyl having 3 to 5 carbons provided that the triple bond is not adjacent to the nitrogen to which $R^1$ is attached, hydroxyalkyl having 2 to 4 carbons in the alkyl portion, optionally substituted alkyl having 1 to 4 carbons, optionally substituted benzyl, optionally substituted cyoloalkyl having 3 to 7 carbons, and alkoxyalkyl having 2 to 4 carbons in the alkyl portion and 1 to 4 carbons in the alkoxy portion and

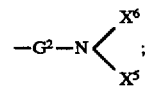

wherein the optionally substituted benzyl is optionally substituted with 1 to 5 substituents selected from the group consisting of $(C_1-C_4)$alkyl, $(C_1-C_4)$alkoxy, fluoro, chloro, bromo, iodo, nitro, amino, cyano, hydroxy, trifluoromethyl and carboalkoxy having 1 to 4 carbons; and the optionally substituted alkyl and optionally substituted cycloalkyl are optionally substituted with cyano, N-alkylamino having 1 to 5 carbons and N,N-dialkylamino having a total of 2 to 6 carbons;

$G^2$ is $(C_2-C_4)$alkylene;

$X^5$ is selected from the group consisting of hydrogen, alkyl having 1 to 4 carbons, cycloalkyl having 3 to 8 carbons and alkoxyalkyl having 2 to 4 carbons in the alkyl portion and 1 to 4 carbons in the alkoxy portion; and $X^6$ is selected from the group consisting of alkyl having 1 to 4 carbons, an optionally substituted hydroxyalkanoyl having 1 to 6 carbons, an aminoacyl group and a dipeptidyl group, the optionally substituted hydroxyalkanoyl group is optionally substituted with an optionally substituted phenyl group wherein the optionally substituted phenyl is optionally substituted with 1 to 5 substituents selected from the group consisting of $(C_1-C_4)$alkyl, $(C_1-C_4)$alkoxy, fluoro, chloro, bromo, iode, nitro, amino, cyano, hydroxy, trifluoromethyl and carboalkoxy having 1 to 4 carbons;

or $X^5$ and $X^6$ are taken together with the nitrogen to which they are attached and form a cyclic amine having 3 to 6 carbon atoms;

or $R^1$ and $R^2$ are taken together with the nitrogen to which they are attached and form

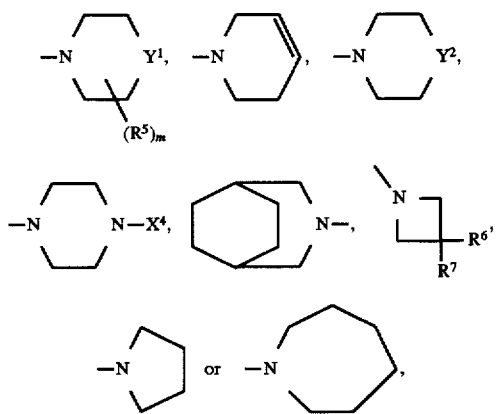

where $Y^1$ is selected from the group consisting of C, CH, $CH_2$, N or NH;
$Y^2$ is O or S;
m is 0, 1 or 2;
$R^5$ is alkyl having 1 to 4 carbons,

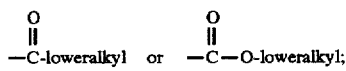

$R^6$ is H or alkyl having 1 to 4 carbons;
$R^7$ is H, alkyl having 1 to 4 carbons, hydroxy, alkoxy having 1 to 3 carbons, amine, N-alkylamino having 1 to 4 carbons or N,N-dialkylamino having a total of 2 to 6 carbons;
or $R^6$ and $R^7$ are taken together and form an oxo; and
$X^4$ is independently selected from the same group as $X^6$.

The term "alkyl" is meant to encompass both straight chain and branched alkyls. The term "loweralkyl" denotes an alkyl group having 1 to 4 carbons. Those skilled in the art will recognize that some of the compounds of the present invention possess stereochemical centers. For those compounds where stereochemical centers are present it is understood that the diastereomeric mixtures as well as the separated diastereomers of the stereochemical compounds are all within the scope of this invention. New double bonds formed, especially at the C-20 position, are formed having the E or Z geometry or a mixture thereof, these geometric isomers are also within the scope of this invention.

As will be readily apparent to one skilled in the art, when $X^1$ is an optionally substituted group consisting of pyridinyl, quinolinyl, isoquinolinyl, quinazolinyl, pyrimidinyl, imidazolyl, oxazolyl, thiazolyl, benzimidazolyl, indolyl, benzoxazolyl and benzthiazolyl, the O or S, to which $X^1$ is attached, cannot be attached to the optionally substituted group through a heteroatom of the ring.

The aminoacyl groups are derivatives of the corresponding amino acids and are well known in the art. The following D- or L- amino acids, where applicable, are used to derive the aminoacyl groups of this invention: alanine, arginine, asparagine, aspartic acid, cysteine, cystine, glutamic acid, glutamine, glycine, histidine, hydroxyllysine, hydroxyproline, isoleucine, leucine, lysine, methionine, phenylalanine, proline, serine, threonine, tryptophane, tyrosine, valine, β-alanine, β-lysine, N,N-dimethylglycine, α,α-dimethylglycine, α-aminobutyric acid, 4-hydroxyphenylglycine, phenylglycine, α,α-diaminobutyric acid, ornithine, homoserine, bicine, N,N-diethyl-β-alanine, N,N-dimethyl-γ-aminobutyric acid, and sarcosine.

The dipeptidyl groups comprise derivatives of any possible combination of two of the amino acids listed hereinabove which have been coupled by conventional methods well known to those skilled in the art.

The hydroxyalkanoyl groups are derivatives of the corresponding hydroxyalkanoic acids and are well known in the art. A few examples of such groups, which are listed for illustration purposes and are not intended to limit the scope of the group, are glycolic acid, lactic acid and mandelic acid.

A group of preferred compounds are those compounds having the formula I wherein n is 1 or 2, $R^1$ is methyl and $R^2$ is methyl or $R^1$ and $R^2$ are taken together with the nitrogen to which they are attached and form pyrrolidinyl or piperidinyl, or $R^1$ is methyl and $R^2$ is

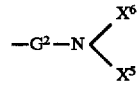

wherein $G^2$ is propylene, $X^5$ is methyl and $X^6$ is methyl, or $X^5$ and $X^6$ are taken together with the nitrogen to which they are attached and form pyrrolidinyl or piperidinyl, Q is selected from the group consisting of dimethylamino, 1,2,3,6- tetrahydropyridinyl and homopiperidinyl, and Z is OH.

An even more preferred group of compounds have the formula I wherein n is 1 and the substituents are as described immediately above for the group of preferred compounds.

Another group of preferred compounds are those compounds having the formula I wherein n is 1, $R^1$ is hydrogen or methyl and $R^2$ is

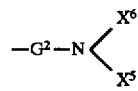

wherein $G^2$ is propylene, $X^5$ is methyl and $X^6$ is methyl. A particularly preferred group of compounds within the immediately recited group of compounds are those wherein Q is 1,2,3,6-tetrahydropyridinyl and Z is OH.

Still another group of preferred compounds are those compounds having the formula I wherein n is 1, $R^1$ is hydrogen or L-alanyl and $R^2$ is

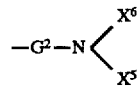

wherein $G^2$ is ethylene or propylene, $X^5$ is methyl and $X^6$ is methyl. A particularly preferred group of compounds within the immediately recited group of compounds are those wherein Q is hydrogen and Z is hydrogen.

DETAILED DESCRIPTION OF THE INVENTION

The compounds of the present invention, having the formula I or II, as defined above, are readily and generally prepared by Wittig reaction of the appropriate macrolide, repromicin, rosaramicin, 5-mycaminosyltylonolide, desmycosin, lactenocin, O-demethyllactenosin, 4'-deoxymycaminosyltylonolide or 23-deoxymycaminosyltylonolide, with an amine containing a Wittig ylide, optionally followed by conversion to the acid addition salt as detailed below.

Derivatization of the parent macrolide at the C-23 position is carried out according to the method well known to those skilled in the art and as described in J. Antibiotics, 40(6), pp. 823–842, 1987, the contents of which are incorporated herein by reference.

The following procedure is used for a Wittig reaction at the C-20 position. To a solution of excess phosphonium bromide (usually 3-fold excess over the macrolide), prepared as described below, in a reaction inert solvent such as toluene, is added an equimolar amount of base, such as potassium bis(trimethylsilyl)amide, 0.5M in toluene. The reaction mixture is stirred for about 5 to 90 minutes, usually for about 15 minutes, at about 5° to 35° C., usually at ambient temperature. To the yellow-orange mixture is added solid macrolide, followed by stirring at about 0° to 80° C., usually at ambient temperature. After having been stirred for about 30 minutes to 24 hours, preferably about one hour, the desired C-20 olefin product is isolated by standard techniques well known to those skilled in the art, such as silica gel chromatography or recrystallization.

The phosphonium bromide reagents used for the above Wittig reactions can be prepared by a number of methods. (2-Aminoethyl)triphenylphosphonium bromides generally are synthesized by reacting a secondary amine with vinyltriphenylphosphonium bromide, usually without additional solvents, and stirring the mixture at about 50° to 150° C., usually at about 80° C., for 0.5 to 3 days, usually for one day. (Procedure modified from J. Org. Chem. 29, pp. 1746–1751, 1964). At this time, the reaction mixture is mixed with an aprotic solvent, preferably diethyl ether, and the solids collected by filtration and rinsed well with the same solvent. Subsequent to drying, these products were used directly in the subsequent olefination procedures. Another route to obtaining amine-containing phosphonium bromides is by treating an appropriate amino alcohol with triphenylphosphine hydrobromide (Helv. Chim. Acta, 61, pp. 1708–1720, 1978). Some of the phosphonium bromides are commercially available.

Phosphonium bromides can also be prepared using diamines, usually with one of the amines protected, with t-BOC as one of the preferred protecting groups. Subsequent to Wittig olefination, the BOC group can be removed by conventional methods and the newly exposed amine can be further functionalized with an aminoacyl, dipeptidyl, or hydroxyalkanoyl group according to the following procedure. A dichloromethane solution of a N-protected amino acid, or N-protected dipeptide (t-BOC is one of the preferred protecting groups), or an O-protected hydroxyalkanoic acid (acetate is one of the preferred protecting groups), dicyclohexylcarbodiimide and hydroxybenzotriazole (all of which are present in equimolar amounts) is cooled to about 0° C. To the cold solution is added a macrolide derivative wherein $X^5$ is as defined above and $X^6$ is H. The solution is allowed to warm to room temperature and stirring is continued for about 6 to 72 hours. The crude product is isolated by conventional methods such as chromatography. The N-protected aminoacyl, N-protected dipeptidyl, or O-protected hydroxyalkanoyl derivative is deprotected by conventional methods to yield desired products.

The pharmaceutically acceptable acid addition salts of the C-20 olefin macrolide derivatives can be obtained by the following general procedure. For example, the HCl salts can be isolated by dissolving the C-20 olefin macrolide derivative in a methanolic HCl solution and then evaporating the volatile components to yield the desired salt. The methanolic HCl solution can be prepared by mixing acetyl chloride with methanol. In addition to the HCl salts, other preferred pharmaceutically acceptable acid addition salts include citrate, phosphate, sulfate, methanesulfonate, palmitate, succinate, lactate, malate, maleate, tartrate, besylate, fumarate and stearate salts. All of such salts are prepared in a method analogous to the method used to form the HCl salt, that is, by mixing equimolar amounts of the acid and base in methanol or methanol/water and then evaporating the solvents.

Rosaramicin is produced and isolated according to the method described by Wagman et al. in Journal of Antibiotics, Vol. XXV, No. 11, pp. 641–646, November 1972. Repromicin is synthesized from rosaramicin using the method taught by Ganguly et al. in U.S. Pat. No. 3,975,372. Desmycosin, lactenocin, O-demethyllactenosin and 23-deoxymycaminosyltylonolide are produced and isolated according to the method described in Journal of Antibiotics, 35(12), pp. 1675–1682, 1982. The contents of the above references are incorporated herein by reference. All other starting materials and reagents required for the synthesis of the compounds of the present invention are readily available according to this invention, commercially or can be prepared according to methods known in the art.

The antibacterial activity of the compounds of the present invention against bacterial pathogens is demonstrated by the compound's ability to inhibit growth of *Pasteurella multocida* and *Pasteurella haemolytica*. The following procedures are typical assays. Assay I is utilized to test for activity against *Pasteurella multocida* and Assay II is utilized to test for activity against *Pasteurella haemolytica*.

ASSAY I (*P. multocida*)

This assay is based on the liquid dilution method in microliter format. A single colony of *P. multocida* (strain 59A067) is inoculated into 5 ml of brain heart infusion (BHI) broth. The test compounds are prepared by solubilizing 1 mg of the compound in 125 µl of dimethylsulfoxide (DMSO). Dilutions of the test compound are prepared using uninoculated BHI broth. The concentrations of the test compound used range from 200 µg/ml to 0.098µg/ml by two-fold serial dilutions. The *P. multocida* inoculated BHI is diluted with uninoculated BHI broth to make a $10^4$ cell suspension per 200 µl. The BHI cell suspensions are mixed with respective serial dilutions of the test compound, and incubated at 37° C. for 18 hours. The minimum inhibitory concentration (MIC) is equal to the concentration of the compound exhibiting 100% inhibition of growth of *P. multocida* as determined by comparison with an uninoculated control.

ASSAY II (*P. haemolytica*)

This assay is based on the agar dilution method using a Steers Replicator. Two to five colonies isolated from an agar plate are inoculated into BHI broth and incubated overnight at 37° C. with shaking (200 rpm). The next morning, 300 µl of the fully grown *P. haemolytica* preculture is inoculated into 3 ml of fresh BHI broth and is incubated at 37° C. with shaking (200 rpm). The appropriate amounts of the test compounds are dissolved in ethanol and a series of two-fold serial dilutions are prepared. Two ml of the respective serial dilution is mixed with 18 ml of molten BHI agar and solidified. When the inoculated *P. haemolytica* culture reaches 0.5 McFarland standard density, about 5 µl of the *P. haemolytica* culture is inoculated onto BHI agar plates containing the various concentrations of the test compound using a Steers Replicator and incubated for 18 hours at 37° C. Initial concentrations of the test compound range from 100–200/µg/ml. The MIC is equal to the concentration of the test compound exhibiting 100% inhibition of growth of *P. haemolytica* as determined by comparison with an uninoculated control.

The in vivo activity of the compounds of formula I or II can be determined by conventional animal protection studies well known to those skilled in the art, usually carried out in mice.

Mice are allotted to cages (10 per cage) upon their arrival, and allowed to acclimate for a minimum of 48 hours before being used. Animals are inoculated with 0.5 ml of a $3\times10^3$ CFU/ml bacterial suspension (*P. multocida* strain 59A006) intraperitoneally. Each experiment has at least 3 non-medicated control groups including one infected with 0.1× challenge dose and two infected with 1× challenge dose; a 10× challenge data group may also be used. Generally, all mice in a given study can be challenged within 30–90 minutes, especially if a repeating syringe (such as a Cornwall® syringe) is used to administer the challenge. Thirty minutes after challenging has begun, the first compound treatment is given. It may be necessary for a second person to begin compound dosing if all of the animals have not been challenged at the end of 30 minutes. The routes of administration are subcutaneous or per os. Subcutaneous doses are administered into the loose skin in the back of the neck whereas oral doses are given by means of a feeding needle. In both cases, a volume of 0.2 ml is used per mouse. Compounds are administered 30 minutes, 4 hours, and 24 hours after challenge. A control compound of known efficacy administered by the same route is included in each test. Animals are observed daily, and the number of survivors in each group is recorded on the form provided. The *P. multocida* model monitoring continues for 96 hours (four days) post challenge. Surviving mice are asphyxiated with carbon dioxide at the end of the study.

The $PD_{50}$ is a calculated dose at which the compound tested protects 50% of a group of mice from mortality due to the bacterial infection which would be lethal in the absence of drug treatment.

To implement the methods of this invention, an effective dose of a compound of formula I or II is administered to a susceptible or infected animal by parenteral (i.v., i.m. or s.c.), oral or topical route. The effective dose will vary with the severity of the disease, and the age, weight and condition of the animal. However, the dose will usually range from about 0.25 to about 150 mg/kg, preferably from about 0.25 to about 25 mg/kg.

A suitable vehicle for administering the dose parenterally is a solution of the compound in sterile water, or a solution of the compound in a solvent comprising at least 50% water and a pharmaceutically acceptable cosolvent or cosolvents such as methanol, ethanol, isopropyl alcohol, propylene glycol, glycerol, carbonate esters like diethyl carbonate, dimethyl sulfoxide, N, N-dimethylformamide, N, N-dimethylacetamide, 1-methyl-2-pyrrolidinone, and the like. Suspensions are also suitable vehicles for administering the compounds of this invention. The suspending medium can be, for example, aqueous carboxymethyl cellulose, inert oils such as peanut oil, highly refined mineral oils, aqueous polyvinylpyrrolidone and so forth. Suitable physiologically acceptable adjuvants may be necessary to maintain the compound in suspension. These adjuvants may be chosen from among thickeners such as carboxymethyl cellulose, polyvinylpyrrolidone, gelatin, and the alginates. Surfactants are also useful as suspending agents. These surfactants include: lethicin, alkylphenol polyethylene oxide adducts, naphthalenesulfonates, alkylbenzenesulfonates and polyoxyethylene sorbitan esters. Agents affecting surface tension can also help in making useful suspensions. Such agents include silicone antifoams, sorbitol, and sugars. For intravenous use the total concentration of solutes should be controlled to render the preparation isotonic.

Thus in a further aspect the invention provides pharmaceutical compositions comprising a compound of the formula (I) or (11) or pharmaceutically acceptable salts thereof, together with a pharmaceutically acceptable carrier or diluent.

This invention also provides a method of treating a bacterial infection or a mycoplasmic infection in an animal in need thereof which method comprises administering to said animal a bacterial or mycoplasmic treating amount of a compound of the formula (I) or (11) or a pharmaceutically acceptable salt thereof.

The present invention is illustrated by the following examples, but is not limited to the details thereof.

EXAMPLE 1

23-(Dimethylamino)-23-deoxy-20-[2-(morpholin-1-yl)-ethylidene]-20-deoxo-5-O-mycaminosyltylonolide To a suspension of 2-(morpholin-1-yl) ethyltriphenylphosphonium bromide (410 mg, 0.90 mmol) in 5 ml of toluene at room temperature was added a solution of potassium bis(trimethylsilyl)amide (0.5M in toluene, 2.0 ml, 1 mmol). Most of the solids dissolved as the solution turned bright orange/yellow. Stirring continued for 15 minutes, at which time solid 23-(dimethylamino)-23-deoxy-5-O-mycaminosyltylonolide (187 mg, 0.30 mmol) was added to the reaction mixture. After about one hour at room temperature, the reaction was partitioned between water and ethyl acetate. The layers were separated and the organic extract was washed twice with water and once with saturated aqueous sodium chloride. The organic layer was dried over anhydrous magnesium sulfate, filtered and then evaporated under reduced pressure. The crude product was purified by flash chromatography on silica gel (9/1 $CHCl_3$/MeOH with 0.1% $NH_4OH$) to provide 136 mg (63% yield) of the title compound: m/e 722.

EXAMPLES 2–77

The following examples were synthesized substantially according to the method described in Example 1.

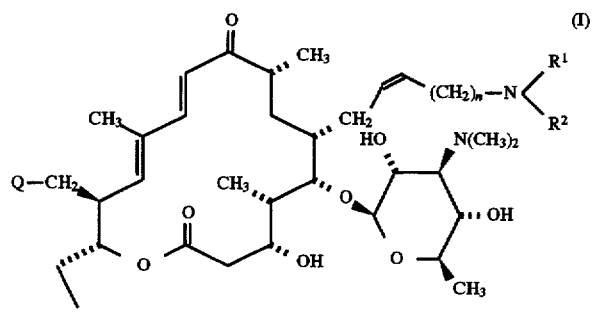

(I)

| Ex. No. | Q | n | NR¹R² | Mass Spec. |
|---|---|---|---|---|
| 2 | 1,2,3,6-tetrahydro-pyridin-1-yl | 1 | dimethylamino | 718 |
| 3 | 1,2,3,6-tetrahydro-pyridin-1-yl | 2 | dimethylamino | 732 |
| 4 | 1,2,3,6-tetrahydro-pyridin-1-yl | 3 | dimethylamino | 747 |
| 5 | 1,2,3,6-tetrahydro-pyridin-1-yl | 1 | pyrrolidino | 745 |
| 6 | 1,2,3,6-tetrahydro-pyridin-1-yl | 1 | piperidino | 758 |
| 7 | 1,2,3,6-tetrahydro-pyridin-1-yl | 1 | morpholino | 760 |
| 8 | 1,2,3,6-tetrahydro-pyridin-1-yl | 1 | 4-methyl-piperazino | 773 |
| 9 | dimethylamino | 1 | pyrrolidino | 707 |
| 10 | 2-hydroxyethyl-methylamino | 1 | pyrrolidino | 736 |
| 11 | 2-hydroxyethyl-methylamino | 1 | morpholino | 752 |
| 12 | morpholino | 1 | dimethylamino | 722 |
| 13 | morpholino | 1 | pyrrolidino | 748 |
| 14 | morpholino | 1 | morpholino | 764 |
| 15 | homopiperidinyl | 1 | dimethylamino | 734 |
| 16 | OH | 1 | dimethylamino | 653 |
| 17 | OH | 1 | pyrrolidino | 679 |
| 18 | OH | 1 | morpholino | 695 |
| 19 | MeO/OMe sugar | 1 | dimethylamino | 827 |
| 20 | MeO/OMe sugar | 1 | pyrrolidino | 854 |
| 21 | MeO/OMe sugar | 1 | morpholino | 869 |
| 22 | dimethylamino | 2 | dimethylamino | 694 |
| 23 | 2-hydroxyethyl-methylamino | 1 | dimethylamino | 710 |
| 24 | MeO/OMe sugar | 1 | N-[3-(dimethyl-amino)-propyl]-N-methylamino | 898 |
| 25 | 1,2,3,6-tetrahydro-pyridin-1-yl | 1 | 1,2,3,6-tetra-hydropyridino | 756 |
| 26 | 1,2,3,6-tetrahydro-pyridin-1-yl (THP) | 1 | homopiperidino | 772 |
| 27 | THP | 1 | thiomorpholino | 776 |
| 28 | THP | 1 | 1-acetylpiperazino | 801 |
| 29 | THP | 1 | bis(2-methoxy-ethyl)amino | 806 |
| 30 | THP | 1 | 3-(dimethyl-amino)propyl-amino | 775 |
| 31 | THP | 1 | N-[3-(methyl-amino)propyl]-N-methylamino | 775 |
| 32 | THP | 1 | 2-(dimethylamino)ethylamino | 761 |
| 33 | THP | 1 | N-[2-(methyl-amino)ethyl]-N-methylamino | 761 |
| 34 | THP | 1 | N-[2-(dimethyl-amino)ethyl]-N-methylamino | 775 |
| 35 | THP | 1 | N-[3-(dimethyl-amino)propyl]-N-methylamino | 789 |
| 36 | 3,3-dimethylpiperidino | 1 | dimethylamino | 748 |
| 37 | phenyl-O | 1 | dimethylamino | 729 |
| 38 | OH | 1 | 4-methyl-piperazino | N.T. |
| 39 | OH | 1 | thiomorpholino | 711 |
| 40 | OH | 1 | 1-acetylpiperazino | 736 |
| 41 | OH | 1 | bis(2-methoxy-ethyl)amino | 741 |
| 42 | OH | 1 | 2-methoxy-ethylamino | 683 |
| 43 | OH | 1 | 1,2,3,6-tetra-hydropyridino | 691 |
| 44 | OH | 1 | homopiperidino | 707 |
| 45 | OH | 1 | N-methylallyl-amino | 679 |
| 46 | OH | 1 | diallylamino | 705 |
| 47 | OH | 1 | dipropargylamino | 701 |
| 48 | OH | 1 | N-methyl-propargylamino | 676 |
| 49 | OH | 1 | butylamino | 681 |
| 50 | OH | 1 | propylamino | 667 |
| 51 | OH | 1 | N-[3-(dimethyl-amino)propyl]-N-methylamino | 724 |
| 52 | OH | 1 | N-[3-(methyl-amino)propyl]-N-methylamino | 710 |
| 53 | OH | 1 | 3-(dimethyl-amino)propyl-amino | 710 |
| 54 | OH | 1 | 2-(dimethyl amino)ethyl-amino | 696 |
| 55 | OH | 1 | N-[2-(methyl-amino)ethyl]-N-methylamino | 696 |
| 56 | OH | 1 | N-[2-(dimethyl-amino)ethyl]-N-methylamino | 710 |
| 57 | OH | 1 | bis(2-cyanoethyl)-amino | 731 |

-continued

| Ex. No. | Q | n | NR¹R² | Mass Spec. |
|---|---|---|---|---|
| 58 | (structure: OMe, OMe, OH pyranose) | 1 | 2-(dimethyl-amino)ethyl-amino | 870 |
| 59 | (structure: OMe, OMe, OH pyranose) | 1 | N-[2-(methyl-amino)ethyl]-N-methylamino | 870 |
| 60 | dimethylamino | 1 | homopiperidino | 734 |
| 61 | dimethylamino | 1 | thiomorpholino | 738 |
| 62 | dimethyiamino | 1 | bis(2-methoxy-ethyl)amino | 768 |
| 63 | dimethylamino | 1 | N-methylallyl-amino | 706 |
| 64 | dimethylamino | 1 | bis(2-cyano-ethyl)amino | 758 |
| 65 | dimethylamino | 1 | diallylamino | 732 |
| 66 | dimethylamino | 1 | N-methyl propargylamino | 704 |
| 67 | dimethylamino | 1 | 2-methoxyethyl-amino | 710 |
| 68 | dimethylamino | 1 | butylamino | 708 |
| 69 | dimethylamino | 1 | propylamino | 694 |
| 70 | dimethylamino | 1 | N-[3-(dimethyl-amino)propyl]-N-methylamino | 751 |
| 71 | dimethylamino | 1 | N-[3-(methyl-amino)propyl]-N-methylamino | 737 |
| 72 | dimethylamino | 1 | 2-(dimethyl-amino)ethylamino | 723 |
| 73 | dimethylamino | 1 | N-[2-(methyl-amino)ethyl]-N-methylamino | 723 |
| 74 | dimethylamino | 1 | 3-(dimethylamino) propylamino | 737 |
| 75 | dimethylamino | 1 | N-[2-(dimethyl-amino)ethyl]-N-methylamino | 737 |
| 76 | N-[3-(dimethylamino)-propyl]-N-methyl-amino | 1 | dimethylamino | 751 |
| 77 | N-[3-(dimethylamino)-propyl]-N-methyl-amino | 1 | morpholino | 793 |

EXAMPLES 78–90

The following examples were synthesized substantially according to the method described in Example 1.

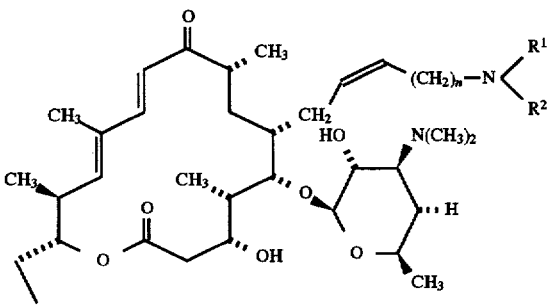

| Ex. No. | n | NR¹R² | Mass Spec. |
|---|---|---|---|
| 78 | 1 | dimethylamino | 621 |
| 79 | 2 | dimethylamino | 635 |
| 80 | 3 | dimethylamino | 649 |
| 81 | 1 | pyrrolidino | 648 |
| 82 | 1 | piperidino | 661 |
| 83 | 1 | morpholino | 663 |
| 84 | 1 | 4-methylpiperazino | 676 |
| 85 | 1 | N-[3-(dimethylamino)-propyl]-N-methylamino | 692 |
| 86 | 1 | 1,2,3,6-tetra-hydropyridino | 659 |
| 87 | 1 | 3-(dimethylamino)-propylamino | 678 |
| 88 | 1 | N-[3-(methylamino)-propyl]-N-methyl-amino | 678 |
| 89 | 1 | 2-(dimethylamino)-ethylamino | 664 |
| 90 | 1 | N-[2-(methylamino)-ethyl]-N-methyl-amino | 664 |

EXAMPLE 91

20-[2-[2-Dimethylaminoethyl(L-alanyl)amino] ethylidene]-20-dexorepromicin

To a solution, of Example 89 (290 mg, 0.44 mmol) in 5 ml of methylene chloride was added triethylamine (0.28 mL, 2.0 mmol) and N-t-Boc-L-alanine (83 mg, 0.44 mmol). The solution was cooled with an ice bath and a 50% solution of propylphosphonic acid cyclic anhydride in methylene chloride (383 mg, 0.60 mmol) was added. After stirring for about 1 h at about 0° C., the reaction was partitioned between water and methylene chloride. The organic layer was washed with saturated aqueous sodium chloride and dried with magnesium sulfate. Filtration and concentration yielded material which was dissolved in 5 mL methylene chloride and cooled to about 0° C. To this solution was added trifluoroacetic acid (1 mL). After about 30 min., the solution was allowed to warm to room temperature and evaporated. The residue was dissolved in saturated aqueous sodium bicarbonate and extracted twice with chloroform. Combined organic layers were washed with saturated aqueous sodium chloride, dried with magnesium sulfate, filtered and concentrated. Title compound was obtained in 80% yield (260 mg, m/e 735).

EXAMPLE 92

20-[2-[2-Methyl(glycyl)aminoethyl(methyl)amino]-ethylidene]-20-deoxorepromicin

The title compound was synthesized substantially according to the procedure of Example 91 using N-t-Boc-glycine and the compound of Example 90 as starting materials. m/e 721.

EXAMPLE 93

23-( 1,2,3,6-Tetrahydropyrid-1-yl)-23-deoxy-20-[2-[3-dimethylaminopropyl(L-alanyl)amino]-ethylidene]-20-deoxo-5-O-mycaminosyltylonolide The title compound was synthesized substantially according to the procedure of Example 91 using N-t-Boc-L-alanine and the compound of Example 30 as starting materials. m/e 846.

EXAMPLE 94

20-[2-Dimethylaminoethylidene]-20-deoxorosaramicin

The title compound was synthesized substantially according to the procedure of Example 1 using 2-(dimethylamino)

ethyltriphenylphosphonium bromide and rosaramicin as starting materials. m/e 637.

PREPARATION 1

4-(Dimethylamino) butyltriphenylphosphonium bromide

Into a solution of 4-dimethylaminobutan-1-ol (2.95g, 25 mmol) and triphenylphosphine (6.55 g, 25 mmol) in benzene (20 ml) was bubbled anhydrous HBr at a moderate rate for about 10 minutes with ice bath cooling. The nearly solid white mass was removed from the cooling bath and heated to about 155° C. for about five hours (benzene distilled off at about 80° C.). After cooling to ambient temperature, water was added to the solid mass and the mixture was filtered to remove insoluble material. The acidic filtrate was extracted three times with chloroform and the aqueous layer was made basic (pH 9) with aqueous saturated NaHCO$_3$, and then concentrated to a white solid. The solids were slurried with chloroform and removed by filtration. The filtrate was dried over magnesium sulfate, filtered, concentrated, and recrystallized from ethanol/ether (1/4). White clusters of needles were obtained and dried under vacuum to afford 5.6 g (51%) of title compound.

PREPARATION 2

2-(Morpholin-1 -yl)ethyltriphenylphosphonium bromide

Vinyltriphenylphosphonium bromide (4.0 g, 10.8 mmol) and morpholine (15 ml) were combined and stirred at about 80° C. for about 3 days. After cooling to ambient temperature, the reaction mixture was poured into 300 ml ether and allowed to granulate. The solids were collected by filtration and dried under vacuum to yield 4.5 g (91%) of desired product.

I claim:

1. A compound of the formula (I)

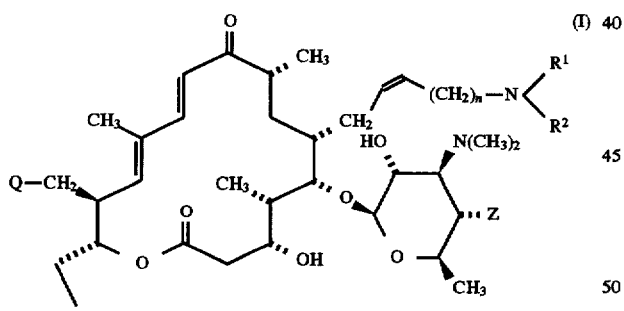

or the formula II

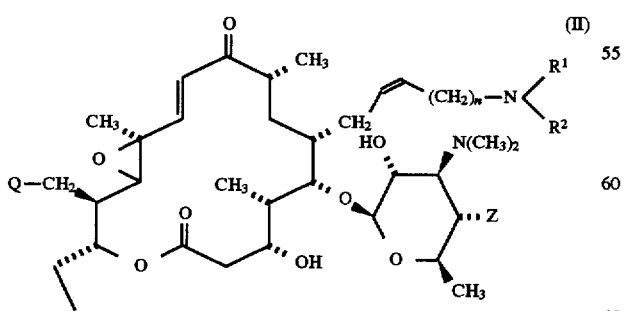

or a pharmaceutically-acceptable salt of the compound of formula (I) or the compound of formula (II) wherein n is an integer from 1 to 4;
Z is H or OH;
Q is selected from the group consisting of H, OH, fluoro, chloro, bromo, iodo, OX$^1$, SX$^1$

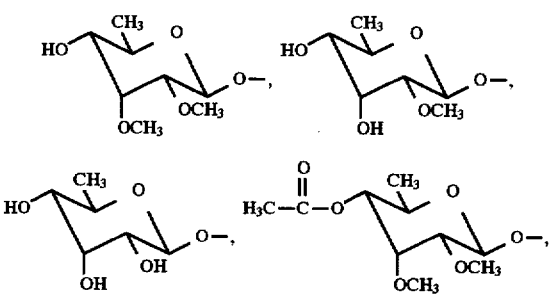

azetidin-1-yl, pyrrolidin-1-yl, piperidin-1-yl, 3,3-dimethylpiperidin-1-yl, hexahydro-azepin-1-yl, octahydroazocin-1-yl, octahydroindol-1-yl, 1,3,3a,4,7,7a-hexahydroisoindol-2-yl, decahydroquinol-1-yl, decahydroisoquinol-2-yl, 1,2,3,4-tetrahydroisoquinol-2-yl, 1,2,3,6-tetrahydropyridin-1-yl, 4-alkylpiperazin-1-yl having 1 to 4 carbons in the alkyl portion, morpholino, 2,6-dimethylmorpholin-4-yl, thiomorpholino, and

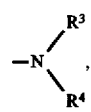

where R$^3$ and R$^4$ are independently selected from the group consisting of H, alkyl having 1 to 4 carbons, hydroxyalkyl having 2 to 4 carbons, cycloalkyl having 3 to 8 carbons, alkenyl having 3 to 4 carbons, optionally substituted benzyl, alkoxyalkyl having 1 to 4 carbons in the alkoxy portion and 2 to 4 carbons in the alkyl portion and alkoxyalkoxyalkyl having 1 to 4 carbons in each of the alkoxy portions and 2 to 4 carbons in the alkyl portion, and

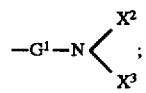

wherein the optionally substituted benzyl is optionally substituted with 1 to 5 substituents selected from the group consisting of (C$_1$–C$_4$)alkyl, (C$_1$–C$_4$) alkoxy, fluoro, chloro, bromo, iodo, nitro, amino, cyano, hydroxy, trifluoromethyl and carboalkoxy having 1 to 4 carbons;

G$^1$ is (C$_2$–C$_4$)alkylene; and

X$^2$ and X$^3$ are independently selected from the group consisting of hydrogen, alkyl having 1 to 4 carbons, cycloalkyl having 3 to 8 carbons, and alkoxyalkyl having 2 to 4 carbons in the alkyl portion and 1 to 4 carbons in the alkoxy portion;

or X$^2$ and X$^3$ are taken together with the nitrogen to which they are attached and form a cyclic amine having 3 to 6 carbon atoms;

X$^1$ is selected from the group consisting of optionally substituted alkyl having 1 to 4 carbons, optionally substituted cycloalkyl having 4 to 8 carbons and an optionally substituted group selected from the group consisting of phenyl, benzyl, pyridinyl, quinolinyl, isoquinolinyl, quinazolinyl, pyrimidinyl, imidazolyl, oxazolyl, thiazolyl, benzimidazolyl, indolyl, benzoxazolyl and benzthiazolyl;

wherein the optionally substituted alkyl and optionally substituted cycloalkyl can be optionally substituted with 1 or 2 substituents independently selected from the group consisting of hydroxy, amino, N-alkylamino having 1 to 4 carbons, N,N-dialkylamino having a total of 2 to 6 carbons and alkoxy having 1 to 4 carbons; and where the optionally substituted group selected from the group consisting of phenyl, benzyl, pyridinyl, quinolinyl, isoquinolinyl, imidazolyl, oxazolyl, thiazolyl, benzimidazolyl, indolyl, benzoxazolyl and benzthiazolyl is optionally substituted with 1 to 3 substituents independently selected from the group consisting of alkyl having 1 to 4 carbons, fluoro, chloro, bromo, amino, nitro, cyano, trifluoromethyl, N-alkylamino having 1 to 4 carbons, N,N-dialkylamino having a total of 2 to 6 carbons, carboxyl, carboalkoxy having 1 to 4 carbons, carboxamido and sulfonamido;

$R^1$ is selected from the group consisting of hydrogen, an aminoacyl group, a dipeptidyl group, alkenyl having 3 to 5 carbons provided that the double bond is not adjacent to the nitrogen to which $R^1$ is attached, alkynyl having 3 to 5 carbons provided that the triple bond is not adjacent to the nitrogen to which $R^1$ is attached, hydroxyalkyl having 2 to 4 carbons in the alkyl portion, optionally substituted alkyl having 1 to 4 carbons, optionally substituted benzyl, optionally substituted cycloalkyl having 3 to 7 carbons, and alkoxyalkyl having 2 to 4 carbons in the alkyl portion and 1 to 4 carbons in the alkoxy portion;

wherein the optionally substituted benzyl is optionally substituted with 1 to 5 substituents selected from the group consisting of $(C_1-C_4)$alkyl, $(C_1-C_4)$alkoxy, fluoro, chloro, bromo, iodo, nitro, amino, cyano, hydroxy, trifluoromethyl and carboalkoxy having 1 to 4 carbons; the optionally substituted alkyl and optionally substituted cycloalkyl are optionally substituted with cyano, N-alkylamino having 1 to 5 carbons or N,N-dialkylamino having a total of 2 to 6 carbons; and the aminoacyl group and the aminoacyl groups of the dipeptidyl group are independently selected from the group consisting of the D- or L- form, when applicable, of alanyl, arginyl, asparagyl, aspartyl acid, cysteinyl, cystyl, glutamyl acid, glutamyl, glycyl, histidyl, hydroxyllysyl, hydroxyprolyl, isoleucyl, leucyl, lysyl, methionyl, phenylalanyl, prolyl, seryl, threonyl, tryptophyl, tyrosyl, valyl, β-alanyl, β-lysyl, N,N-dimethylglycyl, α,α-dimethylglycyl, α-aminobutyryl, 4-hydroxyphenylglycyl, phenylglycyl, α,γ-diaminobutyryl, ornithyl, homoseryl, bicyl, N,N-diethyl-β-alanyl, N,N-dimethyl-γ-aminobutyryl and sarcosyl;

$R^2$ is selected from the group consisting of hydrogen, alkenyl having 3 to 5 carbons provided that the double bond is not adjacent to the nitrogen to which $R^1$ is attached, alkynyl having to 5 carbons provided that the triple bond is not adjacent to the nitrogen to which $R^1$ is attached, hydroxyalkyl having 2 to 4 carbons in the alkyl portion, optionally substituted alkyl having 1 to 4 carbons, optionally substituted benzyl, optionally substituted cycloalkyl having 3 to 7 carbons, and alkoxyalkyl having 2 to 4 carbons in the alkyl portion and 1 to 4 carbons in the alkoxy portion and

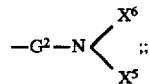

wherein the optionally substituted benzyl is optionally substituted with 1 to 5 substituents selected from the group consisting of $(C_1-C_4)$alkyl, $(C_1-C_4)$alkoxy, fluoro, chloro, bromo, iodo, nitro, amino, cyano, hydroxy, trifluoromethyl and carboalkoxy having 1 to 4 carbons; and the optionally substituted alkyl and optionally substituted cycloalkyl are optionally substituted with cyano, N-alkylamino having 1 to 5 carbons or N,N-dialkylamino having a total of 2 to 6 carbons;

$G^2$ is $(C_2-C_4)$alkylene;

$X^5$ is selected from the group consisting of hydrogen, alkyl having 1 to 4 carbons, cycloalkyl having 3 to 8 carbons and alkoxyalkyl having 2 to 4 carbons in the alkyl portion and 1 to 4 carbons in the alkoxy portion; and $X^6$ is selected from the group consisting of alkyl having 1 to 4 carbons, an optionally substituted hydroxyalkanoyl having 1 to 6 carbons, an aminoacyl group and a dipeptidyl group, wherein the aminoacyl group and the aminoacyl groups of the dipeptidyl group are as defined above for $R^1$; and the optionally substituted hydroxyalkanoyl group is optionally substituted with an optionally substituted phenyl group wherein the optionally substituted phenyl is optionally substituted with 1 to 5 substituents selected from the group consisting of $(C_1-C_4)$alkyl, $(C_1-C_4)$alkoxy, fluoro, chloro, bromo, iodo, nitro, amino, cyano, hydroxy, trifluoromethyl and carboalkoxy having 1 to 4 carbons;

or $X^5$ and $X^6$ are taken together with the nitrogen to which they are attached and form a cyclic amine having 3 to 6 carbon atoms;

or $R^1$ and $R^2$ are taken together with the nitrogen to which they are attached and form

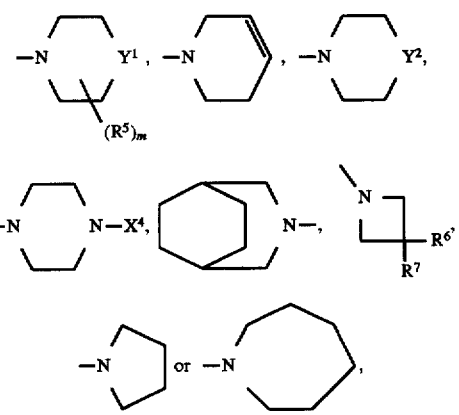

where $Y^1$ is selected from the group consisting of C, CH, $CH_2$, N or NH;

$Y^2$ is O or S;

m is 0, 1 or 2;

$R^5$ is alkyl having 1 to 4 carbons,

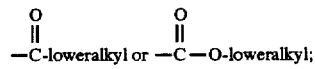

$R^6$ is H or alkyl having 1 to 4 carbons;

$R^7$ is H, alkyl having 1 to 4 carbons, hydroxy, alkoxy having 1 to 3 carbons, amino, N-alkylamino having 1 to 4 carbons or N,N-dialkylamino having a total of 2 to 6 carbons;

or $R^6$ and $R^7$ are taken together and form an oxo; and $X^4$ is independently selected from the same group as $X^6$.

2. A compound according to claim 1 having the formula I, or a pharmaceutically acceptable salt thereof, wherein n is 1 or 2, $R^1$ is methyl and $R^2$ is methyl.

3. A compound according to claim 1 having the formula I, or a pharmaceutically acceptable salt thereof, wherein n is 1 or 2, and $R^1$ and $R^2$ are taken together with the nitrogen to which they are attached and form pyrrolidinyl or piperidinyl.

4. A compound according to claim 1 having the formula I, or a pharmaceutically acceptable salt thereof, wherein n is 1 or 2, $R^1$ is methyl and $R^2$ is

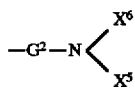

wherein $G^2$ is propylene, $X^5$ is methyl and $X^6$ is methyl.

5. A compound according to claim 1 having the formula I, or a pharmaceutically acceptable salt thereof, wherein n is 1 or 2, $R^1$ is methyl and $R^2$ is

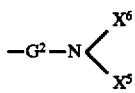

wherein $G^2$ is propylene, $X^5$ and $X^6$ are taken together with the nitrogen to which they are attached and form pyrrolidinyl or piperidinyl.

6. A compound according to claim 2, or a pharmaceutically acceptable salt thereof, wherein Q is selected from the group consisting of dimethylamino, 1,2,3,6-tetrahydropyridinyl and homopiperidinyl and Z is OH.

7. A compound according to claim 3, or a pharmaceutically acceptable salt thereof, wherein Q is selected from the group consisting of dimethylamino, 1,2,3,6-tetrahydropyridinyl and homopiperidinyl and Z is OH.

8. A compound according to claim 4, or a pharmaceutically acceptable salt thereof, wherein Q is selected from the group consisting of dimethylamino, 1,2,3,6-tetrahydropyridinyl and homopiperidinyl and Z is OH.

9. A compound according to claim 5, or a pharmaceutically acceptable salt thereof, wherein Q is selected from the group consisting of dimethylamino, 1,2,3,6-tetrahydropyridinyl and homopiperidinyl and Z is OH.

10. A compound according to claim 6, or a pharmaceutically acceptable salt thereof, wherein n is 1.

11. A compound according to claim 7, or a pharmaceutically acceptable salt thereof, wherein n is 1.

12. A compound according to claim 8, or a pharmaceutically acceptable salt thereof, wherein n is 1.

13. A compound according to claim 9, or a pharmaceutically acceptable salt thereof, wherein n is 1.

14. A compound according to claim 1 having the formula I, or a pharmaceutically acceptable salt thereof, wherein n is 1, $R^1$ is hydrogen or methyl and $R^2$ is

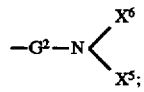

wherein $G^2$ is propylene, $X^5$ is methyl and $X^6$ is methyl.

15. A compound according to claim 14 wherein Q is 1,2,3,6-tetrahydropyridinyl and Z is OH.

16. A compound according to claim 1 having the formula I, or a pharmaceutically acceptable salt thereof, wherein n is 1, $R^1$ is hydrogen or L-alanyl and $R^2$ is

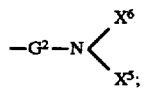

wherein $G^2$ is ethylene or propylene, $X^5$ is methyl and $X^6$ is methyl.

17. A compound according to claim 16 wherein Q is hydrogen and Z is H.

18. A pharmaceutical composition comprising an effective amount of a compound or a pharmaceutically acceptable salt thereof according to claim 1 and a pharmaceutically acceptable carrier.

19. A method of treating a bacterial infection in an animal which comprises administering to said animal a bacterial treating amount of a compound or a pharmaceutically acceptable salt thereof according to claim 1.

20. A method of treating a mycoplasmic infection in an animal which comprises administering to said animal a mycoplasmic treating amount of a compound or a pharmaceutically acceptable salt thereof according to claim 1.

* * * * *